(12) United States Patent
Gaikar et al.

(10) Patent No.: US 6,224,877 B1
(45) Date of Patent: May 1, 2001

(54) PROCESS FOR EXTRACTION OF CURCUMINOIDS FROM CURCUMA SPECIES

(75) Inventors: Vilas Gajanan Gaikar; Deepak Vijay Dandekar, both of Mumbai (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 09/481,842

(22) Filed: Jan. 12, 2000

(30) Foreign Application Priority Data

Sep. 16, 1999 (IN) ...................................... 1241/99

(51) Int. Cl.⁷ .................................................. A01N 65/00
(52) U.S. Cl. ........................................................ 424/195.1
(58) Field of Search .................................. 8/80, 53, 584, 8/607; 426/250, 540, 236.5; 424/195.1

(56) References Cited

U.S. PATENT DOCUMENTS 4,138,212 * 2/1979 Stransky ...................................... 8/80
5,210,316 * 5/1993 Yang et al. ............................ 568/404

OTHER PUBLICATIONS

Gromov, V. Topochemistry of the Hydrotopic Delignification of Birch Wood; Khimiya Drevesiny, No. 15, pp. 16–26. BLL., English Abstract, 1974.*

* cited by examiner

Primary Examiner—Jon P. Weber
Assistant Examiner—Patricia Patten
(74) Attorney, Agent, or Firm—Perkins Coie LLP

(57) ABSTRACT

The present invention relates to a process for extraction of curcuminoids from Curcuma species, which comprises the steps of contacting the rhizome of Curcuma species with an aqueous hydrotrope solution at a temperature in the range of 0–100° C. for extraction of curcuminoids, separating the solution obtained from the solid residue, and recovering the curcuminoids from the solution by known methods.

18 Claims, 2 Drawing Sheets

Figure 1: CROSSSECTION OF C. LONGA RHIZOMES (INTACT)
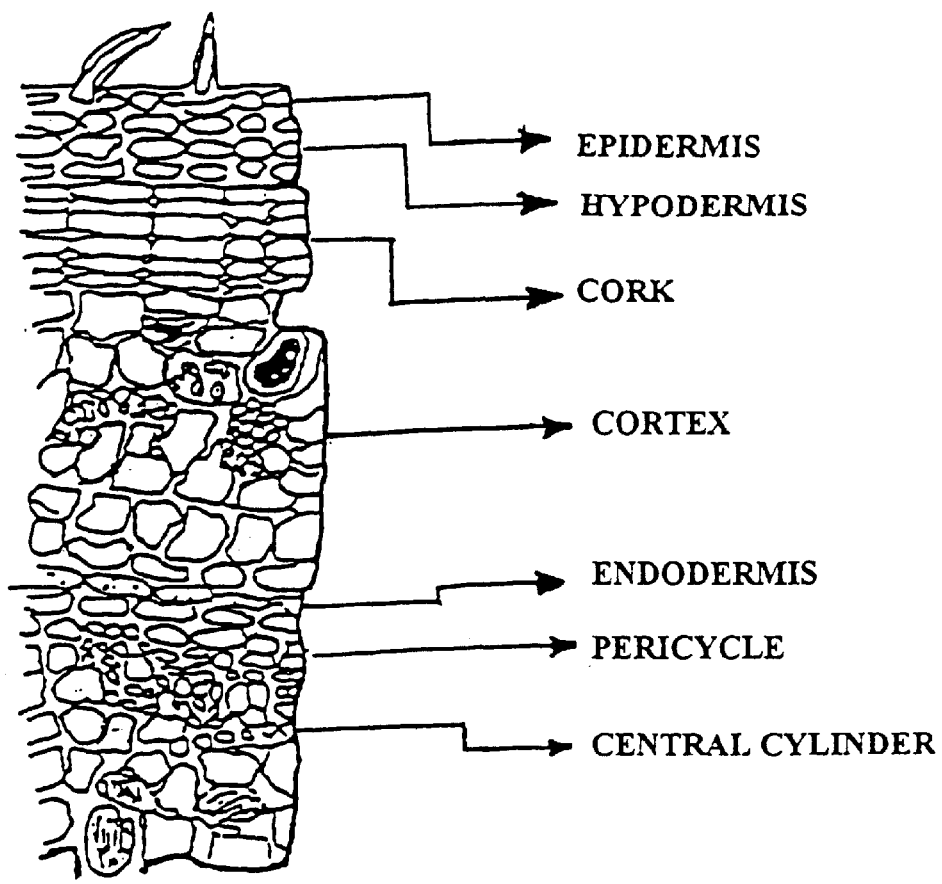

Figure 2: CROSS SECTION OF C. LONGA RHIZOME (DISTORTED)
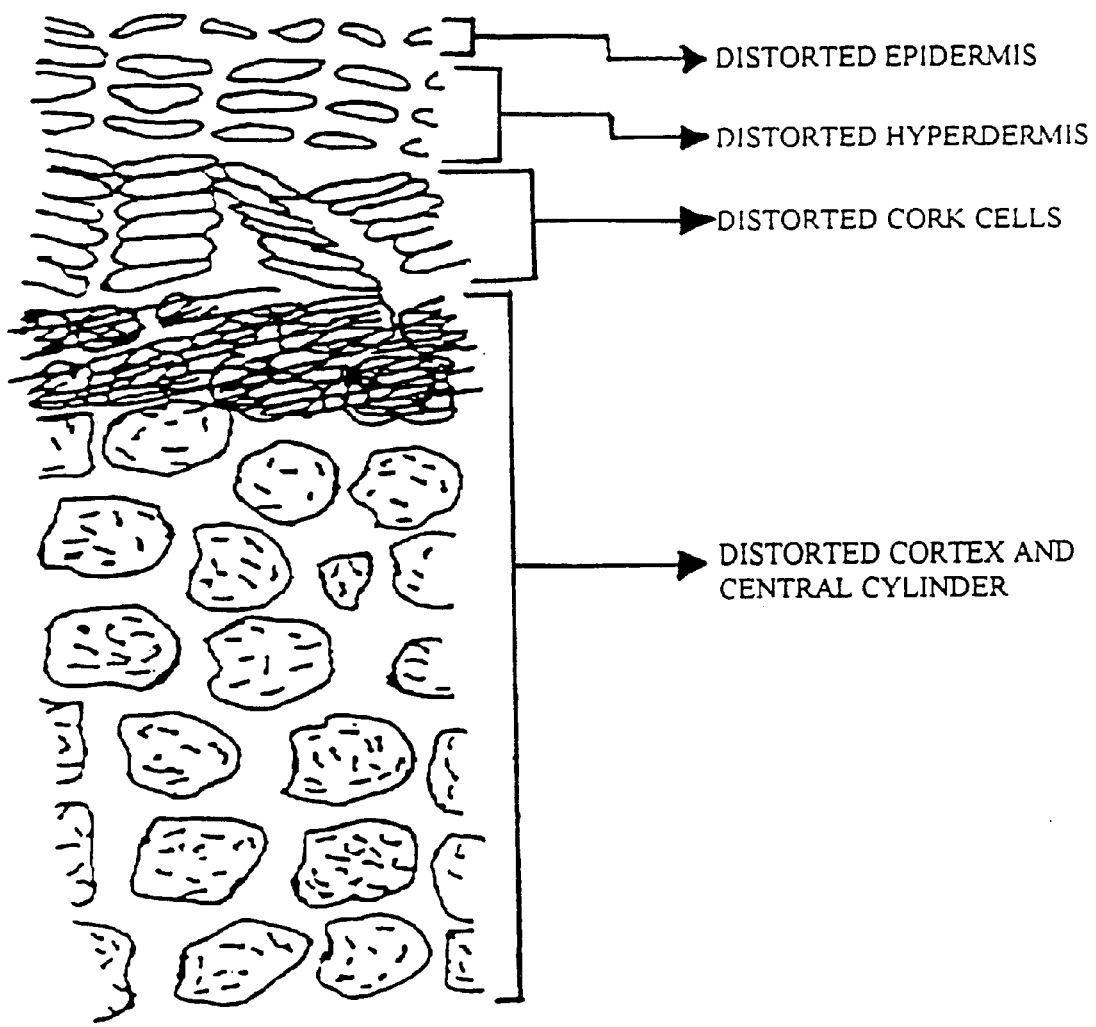

US 6,224,877 B1

PROCESS FOR EXTRACTION OF CURCUMINOIDS FROM CURCUMA SPECIES

FIELD

The present invention relates to a process for extraction of curcuminoids from curcuma species. The present invention particularly relates to extraction of curcumionids using aqueous hydroptrope solutions for the first time.

BACKGROUND

Curcumin ($C_{21}H_{20}O_6$) has many industrial uses. Curcumin is obtained from plants mainly Curcuma. Curcumin, a major constituent of rhizomes of Curcuma species, is present in the form of two related compounds viz. demethoxycurcumin and bisdemethoxycurcumin (together known as curcuminoids). Curcuminoids are used extensively as a food-colouring agent, natural antioxidant, spice, and condiment and for medicinal purposes. It has shown potent anticancer activity [Kuttan, Ramadasan; et. al., Cancer Lett. (Shannon I rel.) 1985, 29(2), 197–202]. Curcuminoids also has potential as an antiviral agent. It has been proven as a modest inhibitor of HIV-1 and HIV-2 proteases [Sui, Z; et. al,. Biorg. Med. Chem. 1993, 6, 415–422].

PRIOR ART RELATING TO THE INVENTION

In the prior art, there are many processes for extraction of curcuminoids from curcuma species. The relevant prior art processes are indicated herebelow:

Sastry B. S. [Res. Ind. 1970, 15, (4), 258–60] described an extraction process for the extraction of curcuminoids from turmeric wherein the curcuminoids were extracted with acetone followed by petroleum ether. Other solvents used for extraction are ethanol, ethyl acetate and benzene. The extraction of curcuminoids into these organic solvents was not very selective, as other compounds like oleoresins were extracted reducing the purity of curcuminoids. This makes post-extraction processing cumbersome.

Myagi, Hisashige et al (Jpn. Kokai Tokyo Koho JP 06,69,479 [9409,479] (CL. C07C49/255), Jan. 18, 1994, Appl. 92/169,647, Jun. 26, 1992; 5pp.) patented a process for extraction of curcuminoids using supercritical carbon dioxide. The supercritical carbon dioxide was actually used for extracting essential oils and then curcuminoids were extracted from *Curcuma longa* using mixture of ethanol and water. This process using supercritical fluid extraction is not economical and curcuminoids extracted is then converted to a water soluble curcumin cyclodextrin complex. Chassagnez, A; et al [Cienc. Technol. Aliment. 1997, 17 (4), 399–404], carried out a pretreatment on *Curcuma longa* material before extraction, using supercritical carbon dioxide and determined that the curcuminoids extraction largely depends on this pretreatment.

Ran, Qiliang; and Zhou, Xianrong [Shipin Kexue (Beijing) 1988, 101, 12–15], extracted curcuminoids from Curcuma with alkaline water (pH~9). The curcuminoids was recovered by precipitation at pH 3–4. The product contained 82.5% curcuminoids. However, the curcuminoids were unstable in alkaline conditions and the degradation rate rapidly increases from pH 7.45 to a maximum of about 10.2.[Price Lisa C; and Buescher. R. W; J. Food Sci. 1997, 62 (2), 267–269].

Most of these prior art processes relate to the extraction of *Curcuma longa* oleoresin containing curcuminoids and other volatile oils. Curcuminoids containing oleoresin is then solvent extracted and recrystallised to obtain pure curcuminoids. These conventional processes are carried out using a number of steps that often present difficult operating conditions and result in high cost of production.

SUMMARY

The present invention relates to a process for extraction of curcuminoids from curcuma species using hydrotrope solutions.

OBJECTS

The main object of the present invention is to provide a very effective process for the extraction of curcuminoids from Curcuma species.

Another object is to provide a cost-effective process for the extraction of curcuminoids from Curcuma species in a substantially pure form using the phenomena of hydrotropy.

Yet another object relates to the use a suitable hydrotrope for selective extraction of curcuminoids from Curcuma species followed by dilution of the extract phase to precipitate curcuminoids in pure form.

Still another object is to provide a simple two step process for the selective extraction of phytochemicals like curcuminoids which successfully exploits the ability of hydrotropes to dissolve the otherwise water insoluble organic compounds in aqueous solution.

One more object is to provide a process for the extraction of curcuminoids from *Curcuma longa* in the first step without using an organic solvent or excessive temperature to retain the purity of curcuminoids.

DETAILED DESCRIPTION

To meet the above objects and the others, the present invention for the first time proposes a very efficient process for the extraction of curcuminoids from Curcuma species. In other words, the present invention provides a cost-effective process for the extraction of curcuminoids from Curcuma species in a substantially pure form using the phenomena of hydrotropy. The present approach is directed to find a suitable hydrotrope for selective extraction of curcuminoids from Curcuma species followed by dilution of the extract phase to precipitate curcuminoids in pure form.

Preferably, the object of the invention is to provide a simple two step process for the selective extraction of phytochemicals like curcuminoids which successfully exploits the ability of hydrotropes to dissolve the otherwise water insoluble organic compounds in aqueous solution. The first step involves the selective extraction of curcuminoids from Curcuma species and its solubilization in the aqueous hydrotrope solution. The second step involves the recovery of curcuminoids by simple dilution with water as most of the curcuminoids precipitates out.

In another embodiment of the invention, the extracted curcuminoids is recovered from the aqueous hydrotrope solution by extraction with an organic solvent followed by desolventisation.

In yet another embodiment, the present process provides extraction of curcuminoids from *Curcuma longa* in the first step without using an organic solvent or excessive temperature to retain the purity of curcuminoids.

The Curcumin of Formula 1, de-methoxy curcumin of Formula 2 and bis (de-methoxy ) curcumin of Formula 3 together known as curcuminoids have been extracted from the rhizomes of Curcuma species.

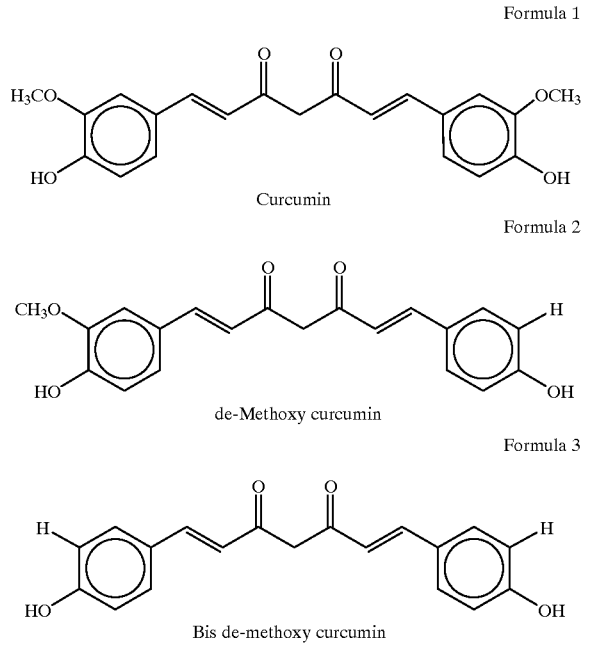

Formula 1 Curcumin
Formula 2 de-Methoxy curcumin
Formula 3 Bis de-methoxy curcumin Accordingly, the present invention provides a process for the extraction of curcuminoids from Curcuma species, which comprises:

(i) contacting Curcuma species with an aqueous hydrotrope solution at a temperature in the range of 0–100° C. for preferential extraction of curcuminoids from the Curcuma species and separating the solution obtained from the solid, and (ii) recovering the curcuminoids from the solution obtained at the end of step (i) by known methods.

In an embodiment, the methods for recovery of curcuminoids from the solution obtained at the end of step (i) are selected from extraction or dilution method.

The rhizomes of Curcuma species such as *Curcuma longa* and *Curcuma aromatica* in pulverized form, preferably in the mesh size of 5 to 300 are brought in intimate contact with an aqueous solution of hydrotrope in the form of a slurry in a stirred vessel. In the process of invention when the contacting is done in the stirred vessel the Curcuma species powder is added to the aqueous hydrotrope solution of concentration in the range of 0.1 mol/L to 5.0 mol/L. After the aforementioned components are brought together the mixture usually in the form of slurry is agitated for a period sufficient for the extraction of curcuminoids to take place. A typical mixing time is in the range of 15 minutes to 24 hours depending upon the concentration of hydrotrope and the speed of agitation. The mixing is conducted at a selected temperature from 0° C.–100° C. preferably at room temperature of 30° C. and atmospheric pressure.

In an embodiment of the invention the curcuminoids are recovered from the aqueous solution of hydrotrope obtained in step (i), after dilution with water or without dilution, by extraction with an organic solvent selected from the group of aromatic and aliphatic hydrocarbons such as benzene, alkylated benzene, heptane, hexane, octane, cyclohexane, halogenated hydrocarbons, ketones, methyl isobutyl ketone, esters such as ethylacetate, propylacetate, ethers such as diethyl ether, diisopropyl ether, dibutyl ether, alcohols such as butanol, hexanol, amides such as phosphoamides, trioctyl phosphene, or mixtures thereof.

The Curcuma species for the extraction of curcuminoids may be selected from *Curcuma longa, Curcuma aromatica, Curcuma amada, Curcuma zedoariai, Curcuma xanthorrhiza, Curcuma caesia, Curcuma aerugiosa, Curcuma angustifolia, Curcuma leucorrhiza, Curcuma pierreana, Curcuma domestica*, and *Curcuma mangga*.

The term "hydrotrope" indicates short alkyl chain water soluble ampiphillic compounds. The hydrotrope is selected from the group comprising sodium, potassium, calcium, ammonium, magnesium salts of alkyl benzene sulfonates, such as benzene sulfonate, toluene sulfonate, xylene sulfonate, ethyl benzene sulfonate, styrene sulfonate, pseudocumene sulfonate, mesitylene sulfonate, propyl benzene sulfonate and butyl benzene sulfonate, alkyl polyglycol sulfates and phosphates such as methyl cellosolve sulfate, ethyl cellosolve sulfate, propyl cellosolve sulfate, butyl cellosolve sulfate, pentyl cellosolve sulfate, hexyl cellosolve sulfate and the corresponding phosphates with sodium, potassium, and calcium counterions; methyl diglycol sulfates, ethyl diglycol sulfates, propyl diglycol sulfates, butyl diglycol sulfates, pentyl diglycol sulfates, hexyl diglycol sulfates and phosphates salts with of sodium, potassium, calcium and ammonium counterions; substituted aromatic carboxylates such as hydroxybenzotaes, toluates, chlorobenzoates, nitrobenzoates, alkyl benzene carboxylates sodium, potassium, calcium and ammonium counterions; substituted phenates, such as hydroxyphenates, chlorophenates, alkyl phenates, naphthols; naphthalene carboxylates; substituted naphthalene carboxylates such as hydroxy naphthalene carboxylates and alkali metal saccharine such as sodium saccharine.

After the mixing the solid residue is separated from the solution by decantation or filtration or by centrifugation. The separated residue is washed with water and the washing is combined with filtrate or the filtrate is used as such for the recovery of curcuminoids.

The filtrate is diluted with water to bring the concentration of hydrotrope low enough to precipitate curcuminoids from the solution. The dilution is done at a temperature at a range 0–80° C. preferably in the range 20–30° C. The precipitated curcuminoids are separated from the solution by decantation or filtration or centrifugation. The curcuminoids are washed with water and dried. The hydrotrope solution recovered during this step is concentrated and recycled.

In another embodiment of this invention the filtrate obtained after the step(i) is subjected to extraction with an organic solvent for recovery of curcuminoids from the aqueous solution of hydrotrope after dilution of the hydrotrope solution with water or without dilution. The organic solvent selected for the extraction may be immiscible with water such as a group consisting of aromatic hydrocarbons, aliphatic hydrocarbons, halogenated hydrocarbons, ketones, ethers, esters, alcohols, amides and a mixtures thereof.

These and other embodiments of the invention are illustrated by the description given hereinbelow supported by the following accompanying drawings wherein:

FIG. 1 represents the cross section of *Curcuma longa* (Turmeric) rhizome showing various cell layers of the rhizome.

FIG. 2 represents the hydrotrope action on cork cells monitored by microscopic studies of several section of rhizomes.

The following portion clearly describes the structures of *Curcuma longa* and the changes brought in by the step of hydrotropes.

A cross section of *Curcuma longa* (Turmeric) rhizome shows various cell layers of rhizomes (FIG. 1). The epidermis is outmost layer, made-up of tangential oblong-rectangular cells. The layer is followed by hypodermis, made-up of two or three layers of irregular shaped parenchymatous cells. The third layer consists of about six layers of tangential oblong-rectangular cork cells arranged in orderly radial rows. The cork cell layer covers cortex and further inner parts. The cortex consists of thin-walled parenchyma cells containing starch, oleoresin cells containing curcuminoids and vascular bundles. Cortex is followed by endodermis containing tangential oblong-rectangular cells in which globules of oil are present. Pericycle, next to endodermis, is also made-up of a layer of tangential oblong-rectangular cells. The innermost part is known as central cylinder consisting of vascular bundle zone adjoining the pericycle, parenchyma cells containing starch, oleoresin cells and vascular bundle scattered in the central tissue region.

The curcuminoids are present in the oleoresin cells, which are present in cortex and central cylinder. The cork cells covering cortex is composed of inner and outer cellulose layers and a median suberin lamella. The mature cork cell is dead and impermeable to water.

In the hydrotropic extraction of turmeric, turmeric rhizomes was pulverized to obtain certain mesh size powder. In the process the outer covering of epidermis, hypodermis and cork cells gets disturbed and the oleoresin cells containing curcuminoids can be directly exposed to hydrotrope solution.

The hydrotrope action on cork cells was monitored by microscopic studies of several section of rhizomes (FIG. 2). The inner part was also exposed directly to aqueous hydrotrope solutions to monitor the hydrotrope effect on the oleoresin cells.

The cell wall structure consists of phospholipid bilayers. The hydrotrope destroys the phospholipid bilayer and penetrates through the cell wall into the inner structures. The proposed process of extraction of curcuminoids therefore utilizes the ability of a hydrotrope molecule to penetrate the cell wall, break the structure and to make curcuminoids available for faster dissolution in the aqueous solutions. The selectivity of the hydrotrope towards the curcuminoids in the cell is probably because of their phenolic structure. The rhizome swells on absorption of water by turmeric cells, swells. The cell wall of cork cells is composed of inner and outer cellulose layers and a median suberin lamella. The suberin lamella makes the cork cell waterproof and thus impermeable to water.

The water soaking shows very less effect on cork cells. But, the hydrotrope solutions break open the organized median suberin lamella and then the mature cork cells. The cork cell layers are disturbed by the hydrotrope. The layers are twisted and the aqueous solution penetrates through the inner parts. The degree of disturbance of the cork cell layers depends on the nature of hydrotrope; cumene sulfonate almost shatters and cork cell layers, BMGS shatters to less extent but more twists are observed, whereas with sodium salicylate or PTSA or sodium saccharine the effect is not prominent.

When the inner part is exposed to the hydrotrope solution, it not only swells the cell, but also frees the. cells from closely bound structures. The effective penetration depends on the nature of the hydrotrope. Cumene sulfonate penetrates the turmeric cells to maximum extent, followed by BMGS, sodium salicylate, PTSA and saccharine sodium in that order. Cumene sulfonate shows the best penetration but less selectivity, whereas BMGS shows higher penetration and high selectivity to curcumin. It also explains the differences in the extraction efficiencies of the different hydrotropes; BMGS gives the highest recovery of curcuminoids with the highest purity followed by sodium salicylate and cumene sulfonate. PTSA and sodium saccharine show moderate penetration and selectivity giving lower yields.

The objects of the invention, its advantages and means of attaining the same are disclosed hereunder in greater detail with reference to the nonlimiting exemplary embodiments of the same. The examples are given by way of illustration only and in no way restrict the scope of the invention.

Chemicals Used:

Curcuma longa (rhizomes of turmeric)

Curcuma aromatica (rhizomes of Curcuma aromatica)

Sodium butyl glycol sulphate (50% aqueous solution, Hulls Germany)

Sodium salicylate (IP grade)

Para-Toluene sulfonic acid (AR grade)

Sodium cumene sulfonate (AR grade)

Sccharine sodium (AR grade)

Dichloromethane (AR grade)

Toluene (AR grade)

Chloroform (AR grade)

Ethanol (AR grade)

Acetic Acid Glacial (AR grade)

Method of Analysis: High Performance Thin Layer Chromatography with E Merck

HPTLC silica plates as stationary phase

EXAMPLE 1

5 gms of pulverized Curcuma longa powder of mesh size #6 was added to 100 ml sodium butyl glycol sulfate 1.0 gmol/lit concentration and stirred vigorously for 8.0 hours at 30° C. The solution was filtered and then diluted by addition of water (100 ml). The precipitated curcuminoids were dried and analyzed for purity. The recovery of curcuminoids was 25.46% (74 mg.) based on the amount of curcuminoids present in the rhizomes with a purity of 94.0%.

EXAMPLE 2

5 gms of pulverized Curcuma longa powder of mesh size #6 was added to 100 ml sodium butyl glycol sulfate 1.5 gmol/lit concentration and stirred vigorously for 8.0 hours at 30° C. The solution was filtered and then diluted by addition of water (200 ml). The precipitated curcuminoids were dried and analyzed for purity. The recovery of curcuminoids was 28.74% (84 mg.) based on the amount of curcuminoids present in the rhizomes with a purity of 93.0%.

EXAMPLE 3

5 gms of pulverized Curcuma longa powder of mesh size #22 was added to 100 ml sodium butyl glycol sulfate 1.5 gmol/lit concentration and stirred vigorously for 8.0 hours at 30° C. The solution was filtered and then diluted by addition of water (200 ml). The precipitated curcuminoids were dried and analyzed for purity. The recovery of curcuminoids was 43.35% (127 mg.) based on the amount of curcuminoids present in the rhizomes with a purity of 92.8%.

EXAMPLE 4

5 gms of pulverized Curcuma longa powder of mesh size #85 was added to 100 ml sodium butyl glycol sulfate 1.5 mol/L concentration and stirred vigorously for 8.0 hours at 30° C. The solution was filtered and then diluted by addition of water (200 ml). The precipitated curcuminoids were dried and analyzed for purity. The recovery of curcuminoids was 36.34% (106 mg.) based on the amount of curcuminoids present in the rhizomes with a purity of 93.4%.

EXAMPLE 5

5 gms of pulverized Curcuma longa powder of mesh size #22 was added to 100 ml sodium butyl glycol sulfate 1.5 mol/L concentration and stirred vigorously for 8.0 hours at 50° C. The solution was filtered at 50° C. and then diluted by addition of water (200 ml) 30° C. The precipitated curcuminoids were dried and analyzed for purity. The recovery of curcuminoids was 51.50% (150 mg.) based on the amount of curcuminoids present in the rhizomes with a purity of 97%.

EXAMPLE 6

5 gms of pulverized *Curcuma longa* powder of mesh size #22 was added to 100 ml sodium butyl glycol sulfate 1.5 gmol/lit concentration and stirred vigorously for 8.0 hours at 50° C. The solution was filtered at 50° C. and diluted by addition of water (200 ml) at 30° C. The precipitated curcuminoids were dried and analyzed for purity. The supernatent solution is then extracted with 300 ml of toluene three times. The recovered curcuminoids was analysed for purity. The total recovery of curcuminoids were 64.76% (189 mg) based on the amount of curcuminoids present in the rhizomes with a purity of 94.97%

EXAMPLE 7

5 gms of pulverized *Curcuma longa* powder of mesh size #6 was added to 100 ml sodium salicylate 3.0 mol/L concentration and stirred vigorously for 8.0 hours at 30° C. The solution was filtered and then diluted by addition of water (400 ml). The precipitated curcuminoids were dried and analyzed for purity. The recovery of curcuminoids was 50.79% (148 mg.) based on the amount of curcuminoids present in the rhizomes with a purity of 89.2%.

EXAMPLE 8

5 gms of pulverized *Curcuma longa* powder of mesh size #22 was added to 100 ml sodium salicylate 3.0 mol/L concentration and stirred vigorously for 8.0 hours at 30° C. The solution was filtered and then diluted by addition of water (400 ml). The precipitated curcuminoids were dried and analyzed for purity. The recovery of curcuminoids was 48.11% (140 mg.) based on the amount of curcuminoids present in the rhizomes with a purity of 90.1%.

EXAMPLE 9

5 gms of pulverized *Curcuma longa* powder of mesh size #85 was added to 100 ml sodium salicylate 3.0 gmol/lit concentration and stirred vigorously for 8.0 hours at 30° C. The solution was filtered and then diluted by addition of water (400 ml). The precipitated curcuminoids were dried and analyzed for purity. The recovery of curcuminoids was 49.79% (145 mg.) based on the amount of curcuminoids present in the rhizomes with a purity of 92.7%.

EXAMPLE 10

5 gms of pulverized *Curcuma longa* powder of mesh size #6 was added to 100 ml sodium salicylate 3.0 mol/L concentration and stirred vigorously for 8.0 hours at 40° C. The solution was filtered and then diluted by addition of water (400 ml). The precipitated curcuminoids were dried and analyzed for purity. The recovery of curcuminoids was 48.67% (142 mg.) based on the amount of curcuminoids present in the rhizomes with a purity of 82.2%.

EXAMPLE 11

5 gms of pulverized *Curcuma longa* powder of mesh size #6 was added to 100 ml para-toluene sulfonic acid 2.0 gmol/lit concentration and stirred vigorously for 8.0 hours at 30° C. The solution was filtered and then diluted by addition of water (1900 ml). The precipitated curcuminoids were dried and analyzed for purity. The recovery of curcuminoids was 13.79% (40 mg.) based on the amount of curcuminoids present in the rhizomes with a purity of 79.3%.

EXAMPLE 12

5 gms of pulverized *Curcuma longa* powder of mesh size #6 was added to 100 ml sodium cumene sulfonate 2.0 mol/L concentration and stirred vigorously for 8.0 hours at 30° C. The solution was filtered and then diluted by addition of water (3900 ml). The precipitated curcuminoids were dried and analyzed for purity. The recovery of curcuminoids was 38.56% (113 mg.) based on the amount of curcuminoids present in the rhizomes with a purity of 90.7%.

EXAMPLE 13

5 gms of pulverized *Curcuma longa* powder of mesh size #6 was added to 100 ml sodium cumene sulfonate 2.0 mol/L concentration and stirred vigorously for 8.0 hours at 30° C. The solution was filtered and then extracted with 200 ml. dichloromethane five times. The recovered curcuminoids was analysed for purity. The recovery of curcuminoids was 28.45% (83 mg.) based on the amount of curcuminoids present in the rhizomes with a purity of 98.2%.

EXAMPLE 14

5 grns of pulverized *Curcuma longa* powder of mesh size #6 was added to 100 ml saccharine sodium 2.0 mol/L concentration and stirred vigorously for 8.0 hours at 30° C. The solution was filtered and then extracted with 200 ml. dichloromethane five times. The recovered curcuminoids was analysed for purity. The recovery of curcuminoids was 17.5% (51 mg.) based on the amount of curcuminoids present in the rhizomes with a purity of 96.3%.

EXAMPLE 15

5 gms of pulverized *Curcuma aromatica* powder of mesh size #6 was added to 100 ml sodium cumene sulfonate 2.0 gmol/lit concentration and stirred vigorously for 8.0 hours at 30° C. The solution was filtered and then diluted by addition of water (3900 ml). The precipitated curcuminoids were dried and analyzed for purity. The recovery of curcuminoids was 46.7% (13 mg.) based on the amount of curcuminoids present in the rhizomes with a purity of 86.1%.

EXAMPLE 16

5 gms of pulverized *Curcuma aromatica* powder of mesh size #6 was added to 100 ml para-toluene sulfonic acid 2.0 mol/L concentration and stirred vigorously for 8.0 hours at 30° C. The solution was filtered and then diluted by addition of water (1900 ml). The precipitated curcuminoids were dried and analyzed for purity. The recovery of curcuminoids was 19.49% (5 mg.) based on the amount of curcuminoids present in the rhizomes with a purity of 61.1%.

EXAMPLE 17

5 gms of pulverized *Curcuma aromatica* powder of mesh size #6 was added to 100 ml sodium cumene sulfonate 2.0 mol/L concentration and stirred vigorously for 8.0 hours at 30° C. The solution was filtered and then extracted with 200 ml. dichloromethane five times. The recovered curcuminoids was analysed for purity. The recovery of curcuminoids was 42.88% (12 mg.) based on the amount of curcuminoids present in the rhizomes with a purity of 97.9%.

EXAMPLE 18

5 gms of pulverized *Curcuma aromatica* powder of mesh size #22 was added to 100 ml sodium butyl glycol sulfate 1.5 mol/L concentration and stirred vigorously for 8.0 hours at 30° C. The solution was filtered and then extracted with 200 ml. dichloromethane five times. The recovered curcuminoids was analysed for purity. The recovery of curcuminoids was 89.12% (24 mg.) based on the amount of curcuminoids present in the rhizomes with a purity of 96.4%.

TABLE 1

Different hydrotropes used for extraction

| Hydrotrope (Sodium Salts) | Curcuminoids | |
|---|---|---|
| | % Extraction | % Purity |
| Butyl mono glycol sulfate (Na-BMGS) | 51.5 | 97.0 |
| Cumene sulfonate (Na-CS) | 38.56 | 90.7 |
| Salicylate (Na-S) | 50.79 | 89.2 |
| p-Toluene sulfonate acid (acid form ($C_p$-TSA) | 13.79 | 79.3 |

In the case of extraction of curcuminoids from *Curcuma longa* it was observed that Na-BMGS and sodium salicylate give optimum yields and good selectivity. Though the selectivity obtained from Na-cumene sulfonte is high the extraction efficiency is very low.

The Main Advantages of the Present Invention are:

A simple practically viable method has been provided for the extraction of curcuminoids.

The number of steps required for extraction have been reduced and simple operating conditions are provided which can reduce the cost of production.

The hydrotrope solution can be recycled with or without the concentration step for further extraction, which reduces the cost of chemicals.

The process of the present invention is carried out preferentially at moderate temperature, which is an improvement over the prior art as it does not degrade curcuminoids and other chemicals.

The first step of the process of the present invention is carried out without the use of any organic solvent which retains the purity of curcuminoids and is an improvement over the prior art.

What is claimed is:

1. A process for extraction of curcuminoids from Curcuma species comprising the steps of:
   (i) contacting the rhizomes of Curcuma species with an aqueous hydrotope at a temperature in the range of 0–100° for preferential extraction of curcuminoids from Curcuma species to obtain a mixture;
   (ii) separating solid residue from the mixture to obtain a solution; and
   (iii) recovering the curcuminods from the solution obtained from step (ii) by known methods.

2. A process as claimed in claim 1 wherein the hydrotrope in step (i) is selected from the group consisting of alkali metal salts of alkyl benzene sulfonates, alkyl polyglycol sulfates or phosphates, substituted aromatic carboxylates, substituted phenates, substituted naphthonates, substituted naphthalene carboxylates, alkali metal saccharines and naphthols.

3. A process as claimed in claim 2 wherein the alkali metal salts of alkyl benzene sulfonates are selected from the group consisting of sodium, potassium, calcium, magnesium and ammonium.

4. A process as claimed in claim 2 wherein the alkyl benzene sulfonates are selected from the group consisting of benzene sulfonate, toluene sulfonate, xylene sulfonate, ethyl benzene sulfonate, styrene sulfonate, pseudocumene sulfonate, mesitylene sulfonate, propyl benzene sulfonate and butyl benzene sulfonate.

5. A process as claimed in claim 2 wherein the substituted aromatic carboxylates are selected from the group consisting of hydroxybenzoates, toluates, chlorobenzoates, nitrobenzoates, alkyl benzene carboxylates.

6. A process as claimed in claim 2 herein the substituted phenates are selected from the group consisting of hydroxyphenates, chlorophenates, and alkyl phenates.

7. A process as claimed in claim 2 wherein the substituted naphthalene carboxylates are hydroxy naphthalene carboxylates.

8. A process as claimed in claim 2 wherein the alkali metal saccharine is sodium saccharine.

9. A process as claimed in claim 2 wherein the alkyl polyglycol sulfates and phosphates are selected from the group consisting of methyl cellosolve sulfate, ethyl cellosolve sulfate, propyl cellosolve sulfate, butyl cellosolve sulfate, pentyl cellosolve sulfate, hexyl cellosolve sulfate, methyl diglycol sulfates, ethyl diglycol sulfates, propyl diglycol sulfates, butyl diglycol sulfates, pentyl diglycol sulfates, hexyl diglycol sulfates and the corresponding phosphates.

10. A process as claimed in claim 9, wherein the sulphates and phosphates are salts of counterions, wherein the counterions are selected from the group consisting of sodium, potassium, calcium and ammonium.

11. A process as claimed in claim 1 wherein the methods for recovery of curcuminoids from the solution obtained at the end of step (ii) are selected from extraction or dilution.

12. A process as claimed in claim 1 wherein the curcuminoids are extracted from Curcuma species selected from the group consisting of *Curcuma longa, Curcuma aromatica, Curcuma amada, Curcuma zedoariai, Curcuma xanthorrhiza, Curcuma caesia, Curcuma aerugiosa, Curcuma angustifolia, Curcuma leucorrhiza, Curcuma pierreana, Curcuma domestica*, and *Curcuma mangga*.

13. A process as claimed in claim 1 wherein the concentration of hydrotrope is in the range of of 0.1 mol/L to 5.0 mol/L.

14. A process as claimed in claim 1 wherein curcuminoids are recovered from the solution obtained in step (ii) by treating the solution with an organic solvent selected from the group consisting of aromatic and aliphatic hydrocarbons comprising benzene, alkylated benzene, heptane, hexane, octane, cyclohexane, halogenated hydrocarbones, ketones, methyl isobutyl ketone, esters comprising ethylacetate and propylacetate, comprising diethyl ether, diisopropyl ether, dibutyl ether, alcohols comprising butanol, hexanol, and amides comprising phosphoamides, trioctyl phosphene and mixtures thereof.

15. A process as claimed in claim 1 wherein the rhizomes of curcuma species are pulverised to mesh size of about 5 to 300.

16. A process as claimed in claim 1 wherein curcuminoids are recovered from the solution obtained at the end of step (ii) by diluting the solution with water at a temperature in the range of 0–80° C.

17. A process as claimed in claim 1 wherein the mixture obtained in step (i) is agitated for a period of 15 minutes to 24 hrs before separating the solution.

18. A process as claimed in claim 1 wherein the solid residue in step (ii) is separated from the solution by decantation, filtration or centrifugation.

* * * * *